US009722256B1

(12) United States Patent
Serov et al.

(10) Patent No.: US 9,722,256 B1
(45) Date of Patent: *Aug. 1, 2017

(54) IMIDAZOLE-DERIVED MATERIALS

(71) Applicants: Alexey Serov, Albuquerque, NM (US);
Plamen B Atanassov, Santa Fe, NM (US)

(72) Inventors: Alexey Serov, Albuquerque, NM (US);
Plamen B Atanassov, Santa Fe, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,104

(22) Filed: Oct. 7, 2015

Related U.S. Application Data

(63) Continuation-in-part of application No. 14/091,776, filed on Nov. 27, 2013, now Pat. No. 9,180,443.

(60) Provisional application No. 61/730,172, filed on Nov. 27, 2012.

(51) Int. Cl.
*H01M 4/90* (2006.01)
*C07F 15/02* (2006.01)
*H01M 4/88* (2006.01)
*H01M 8/1018* (2016.01)

(52) U.S. Cl.
CPC ......... *H01M 4/9008* (2013.01); *C07F 15/025* (2013.01); *H01M 4/8846* (2013.01); *H01M 2008/1095* (2013.01)

(58) Field of Classification Search
CPC ... B01J 21/00; B01J 23/00; B01J 27/00; B01J 27/20; B01J 27/24; B01J 37/00; B01J 37/0018; B01J 37/0036; B01J 37/0063; B01J 37/082
USPC ................. 502/167, 200, 305–355
See application file for complete search history.

(56) References Cited

U.S. PATENT DOCUMENTS

| 6,545,108 B1 * | 4/2003 | Moody ..................... C07C 2/32 502/167 |
| 9,180,443 B1 * | 11/2015 | Serov ................... B01J 37/0018 |
| 2007/0026292 A1 * | 2/2007 | Adzic .................... B82Y 30/00 429/424 |
| 2010/0167106 A1 * | 7/2010 | Pak ...................... H01M 4/8814 429/525 |
| 2010/0210744 A1 * | 8/2010 | Zhang ................... B01J 20/265 521/50 |
| 2012/0077667 A1 * | 3/2012 | Liu ...................... H01M 4/8605 502/101 |
| 2014/0193730 A1 * | 7/2014 | Martinez ............. H01M 4/9041 429/421 |

FOREIGN PATENT DOCUMENTS

WO WO 2013116754 A1 * 8/2013 ............. B01J 37/08

* cited by examiner

*Primary Examiner* — Patricia L Hailey
(74) *Attorney, Agent, or Firm* — Gonzales Patent Services; Ellen M. Gonzales (57) ABSTRACT

In the present disclosure, imidazole-derived materials including M-N—C catalysts, imidazole-derived MOFs and MOF-based M-N—C catalysts as well as methods for preparing the same utilizing mechanochemical synthesis and/or a sacrificial support-based methods are described.

15 Claims, 7 Drawing Sheets

IMIDAZOLE-DERIVED MATERIALS

CROSS-REFERENCE TO RELATED APPLICATIONS

The following application is a continuation-in-part of U.S. patent application Ser. No. 14/091,776, "Imidazole-Derived Materials" filed Nov. 27, 2013, which claims benefit of U.S. Provisional Application Nos. 61/730,172, filed Nov. 27, 2012, and 61/878,416, filed Sep. 16, 2013, each of which is hereby incorporated by reference in its entirety.

STATEMENT REGARDING GOVERNMENT SPONSORED RESEARCH

This invention was made with Government support under Grant No. 2RQ83 awarded by the DOE-EERE. The U.S. Government has certain rights in this invention.

BACKGROUND

Imidazole is an organic compound having the formula $(CH)_2N(NH)CH$. Imidazole exists in two equivalent tautomeric forms, with the proton located at either of two nitrogen atoms, this also enables it to function as either an acid or a base. Imidazole is used extensively as a corrosion inhibitor Materials containing or derived from imidazole and members of the imidazole family are useful in a variety of applications including, but not limited to fuel cell catalysts, metal organic frameworks (MOFs), ionic liquids, high temperature polymeric membranes and MOF-derived catalysts.

MOFs are compounds formed from metal ions or clusters and organic molecules (usually rigid) to form one-, two- or three-dimensional porous structures. MOFs are commonly used as gas absorbents, $CO_2$ capture and for hydrogen storage, but may also be used as a starting materials for catalytic materials.

Fuel cells are receiving increasing attention as a viable alternative energy conversion technology. In general, fuel cells directly convert electrochemical energy into electrical energy in an environmentally clean and efficient manner. Fuel cells are contemplated as potential energy sources for everything from small electronics to cars and homes. In order to meet different energy requirements, there are a number of different types of fuel cells in existence today, each with varying chemistries, requirements, operation conditions, and uses.

As one example, Direct Methanol Fuel Cells (DMFCs) rely upon the oxidation of methanol on an electrocatalyst layer to form carbon dioxide. Water is consumed at the anode and produced at the cathode. Positive ions ($H^+$) are transported across a proton exchange membrane to the cathode where they react with oxygen to produce water. Electrons can then be transported via an external circuit from anode to cathode providing power to external sources.

As another example, polymer electrolyte membrane (PEM) fuel cells (also called proton exchange membrane fuel cells) use pure hydrogen (typically supplied by a hydrogen tank) as a fuel. A stream of hydrogen is delivered to the anode side of a membrane-electrode assembly (MEA), where it is catalytically split into protons and electrons. As with the DMFC, the positive ions are transported across a proton exchange membrane to the cathode where they react with oxygen to produce water.

Currently, one of the limiting factors in the wide scale commercialization of PEM and DMFC fuel cells is the cost associated with precious metals. Both DMFC and PEM fuel cells commonly use platinum or platinum alloys as an electrocatalyst. Nobel metals such as platinum are needed to catalyze the sluggish oxygen reduction reaction (ORR) at the cathode. One of the major routes to overcome this limitation is to increase the platinum utilization in noble-metal based electrocatalysts. Another viable route is to use a less expensive, yet still sufficiently active catalyst in larger quantities. Several classes of non-platinum group metals (non-PGM) electrocatalysts have been identified as having adequate oxygen reduction activity to be considered as potential electrocatalysts in commercial fuel cell applications.

Generally, known non-platinum electrocatalysts are supported on high surface area carbon blacks. This is done to increase dispersion, active surface area, and conductivity of the catalytic layer. The synthesis procedure usually includes precipitation of the precursor molecules onto the supporting substrate and pyrolysis of the supported precursor.

Metal-Nitrogen-Carbon (M-N—C) catalysts have been found to be very promising for electrochemical oxygen reduction applications in fuel cell membrane electrode assemblies (MEAs), stacks and fuel cell systems. Critical aspects of the materials include the presence of metallic particles, conjugated carbon-nitrogen-oxide-metallic networks, and nitrogen-bonded carbon. The metallic phase includes metallic, oxide, carbide, nitride, and mixtures of these states. The chemical states and bonding of the M-N—C networks and N—C networks influences performance, for example, increased overall nitrogen content improves ORR performance. However, these systems still suffer from several significant drawbacks including: low stability in acidic environments, low durability in acid and alkaline environments, high costs of nitrogen-carbon precursors and low activity in ORR compared with platinum. The problem of low stability in acid is connected to leaching of metal from carbon-nitrogen network which results in degradation of membrane and ionomer in MEA. Low durability in acid and alkaline solutions is explained by the evolution of significant amount of $H_2O_2$ in these environments which is Fenton radical producer resulting in chemical decomposition of ionomer and MEA itself. The low activity is possibly due to the low concentration of active sites in such catalysts due to using external carbon source (medium to high surface carbons like Vulcan, KetjenBlack etc).

Despite the fact that there are several companies working on commercialization of M-N—C catalysts [32-34], the majority of non-PGM catalysts are being synthesized in the researcher's labs in sub-grams amounts. Furthermore, typical synthesis methods usually utilize solvent-based wet impregnation of a carbon support with precursors of a transition metal and a nitrogen-carbon source (complex-forming or chelating agent, polymer precursors or polymers). The estimation of the amount of solvent used for preparation of one kilogram of M-N—C catalysts by the method described is on the order of 200-300 liters, introducing the problem of waste management. In addition to this, some amount of the solvents may stay as a residue during the pyrolysis steps and, thus, contribute to the variability of the synthesis outcome. Furthermore, solvent-based methods necessarily require that the materials used be soluble, preventing the production and development of M-N—C catalysts formed from non-soluble materials.

SUMMARY

In the present disclosure, imidazole-derived materials including M-N—C catalysts, imidazole-derived MOFs and MOF-based M-N—C catalysts as well as methods for preparing the same utilizing mechanochemical synthesis and/or a sacrificial support-based methods are described.

DETAILED DESCRIPTION

According to an embodiment, the present disclosure provides materials including, but not necessarily limited to, imidazole-derived materials including M-N—C catalysts, imidazole-derived MOFs, imidazole-derived ionic liquids and MOF-based M-N—C catalysts and methods for making the same.

According to a more specific example, materials including M-N—C catalysts, imidazole-derived MOFs, and MOF-based catalysts according to the present disclosure may be synthesized by utilizing heat treatment with a (sacrificial) support and/or mechanochemical synthesis and using inexpensive and readily available precursors of imidazole and/or imidazole family members.

As stated above, imidazole is an organic compound having the formula $(CH)_2N(NH)CH$. Imidazole is a heterocycle containing a $1,3-C_3N_2$ ring. Derivatives of imidazole, commonly referred to as imidazoles, contain the $1,3-C_3N_2$ ring but feature varied substituents. Examples of imidazoles include, for example, Imidazole trifluoromethanesulfonate salt, Imidazole-2-carboxylic acid, imidazole-2-boronic acid, 1-(m-Tolyl)imidazole, 1-(3-Aminopropyl)imidazole, 1H-imidazole-4-carbothioamide, benzimidazole (BZIM), AminoBenzImidazole, and MethylImidazole. For the purposes of the present disclosure, members of the imidazole family includes compounds, such as imidazolium salts like imidazolium chloride and imidazolide or imidazolate salts like sodium imidazolide, formed from imidazole or imidazoles. Furthermore, according to some embodiments it may be desirable for the imidazole(s) to be functionalized with the addition of functional groups such as amine, nitro, phenol, extending from nitrogen containing functional groups. For the purpose of brevity, throughout the remainder of the specification numerous embodiments are described that refer to the inclusion of imidazole. It should be understood that many of these embodiments could readily be altered to utilize, incorporate, substitute or otherwise include imidazoles or imidazole family members in addition to or instead of imidazole alone.

According to a first embodiment, the present disclosure provides an inexpensive method for producing M-N—C catalysts and catalytic materials utilizing imidazole as the source of nitrogen and carbon and a transitional metal precursor as the source of metal.

For the purposes of the present disclosure, the term "precursor" is used to refer to a compound which participates in a chemical reaction by contributing one or more atoms to a compound that is formed as the product of the chemical reaction.

For the sake of clarity, in the present application the term "catalyst" is used to refer to a final product, suitable for use, for example, in a fuel cell, which has catalytic activity. The catalyst may include multiple types of materials, some of which may not in themselves have catalytic activity (for example, supporting material). The term "catalytic material" is any material which has catalytic activity either on its own or as part of a catalyst.

In general, the method according to a first embodiment, includes enabling the imidazole and transition metal precursors to interact, and thus form around a supporting material, which may or may not be a sacrificial support, and heat treating the resulting material. If a sacrificial support is used, the method further includes removing the sacrificial support to produce a self-supporting porous material formed from the precursor materials. For the purposes of the present disclosure, the term "sacrificial support" is intended to mean a material which is used during the synthesis process to provide a temporary structural support, but which is removed during the synthesis step and is not included as part of the final material.

It will be appreciated that the supporting material may be synthesized and infused in a single synthesis step or the supporting material may be synthesized first (or otherwise obtained) and then infused, surrounded, or otherwise contacted with the polymerizing imidazole and metal precursors. The resulting material is then subjected to heat treatment, (such as pyrolysis) in an inert ($N_2$, Ar, He, etc.) or reactive ($NH_3$, acetonitrile, etc.) atmosphere.

According to one embodiment, the supporting material is infused, surrounded, or otherwise contact with imidazole and iron precursors. Suitable iron precursors include, but are not limited to, iron nitrate, iron sulfate, iron acetate, iron chloride, etc. Furthermore, it will be appreciated that other transition metals such as Ce, Cr, Co, Cu, Mn, Mo, Ni, Ru, Ta, Ti, V, W, and Zr can be substituted in place of iron, by simply using precursors of those metals instead. Examplary transition metal precursors include, but are not limited to cerium nitrate, chromium nitrate, copper nitrate, ammonium molybdate, nickel nitrate, ruthenium chloride, tantalum isopropoxide, titanium ethoxide, vanadium sulfate, ammonium tungstanate and zirconium nitrate. Furthermore, according to some embodiments the presently described methodologies may utilize precursors of two or more metals to produce multi-metallic catalysts.

Of course it will be appreciated that given the high temperatures that the supporting material will be subjected to during the synthesis method, it is important to select a support which is non-reactive to the catalytic materials under the specific synthesis conditions used. According to some embodiments, silica is a preferred material for use as a sacrificial support, but that other suitable materials may be used. Other suitable material for sacrificial supports include, but are not limited to zeolites, aluminas, clays and the like. The support may take the form of spheres, particles, or other two or three dimensional regular, irregular, or amorphous shapes. The spheres, particles, or other shapes may be monodisperse, or irregularly sized. The spheres, particles, or other shapes may or may not have pores and such pores may be of the same or different sizes and shapes.

Because the sacrificial supports are removed after the imidazole-metal material has formed around it, the shape of the sacrificial supports determines the shape of the voids within the resulting material. It should thus be appreciated that the size and shape of sacrificial particles may be selected according to the desired shape(s) and size(s) of the voids within the resulting material. Accordingly, by selecting the particular size and shape of sacrificial particles, one can produce a final material having voids of a predictable size and shape. For example, if the sacrificial particles are spheres, the resulting material will contain a plurality of spherical voids. Those of skill in the art will be familiar with the electrocatalyst Pt—Ru black, which consists of a plurality of platinum-ruthenium alloy spheres. A material formed with the above-described method using a sphere-shaped sacrificial material will look like a negative image of the Pt—Ru black; the space that existed as a void in the Pt—Ru black will be filled with the resulting material, and the space that existed as metal electrocatalyst in the Pt—Ru black is void.

As stated above, according to some embodiments, particulate supporting materials of any diameter may be used. In some preferred embodiments, particles having a characteristic length of between 1 nm and 100 nm, in more preferred embodiments, particles having characteristic lengths of between 100 nm and 1000 nm may be used, and in other preferred embodiments, sacrificial particles having characteristic lengths of between 1 mm and 10 mm may be used. Further a mesoporous material, such as, but not necessarily limited to, mesoporous silica can also be used in the templating synthesis approach. In one specific example of a method using mesoporous sacrificial material, the templating involves intercalating the mesopores of the sacrificial material and results in a self-supported resulting material with a porosity in the 2-20 nm range.

In one exemplary embodiment, a silica template formed from 20 nm diameter Cabosil amorphous fumed silica (325 $m^2/g$) spheres is used. As stated above, because the spheres serve as the template for the formation of the resulting materials, in an embodiment where sacrificial particles having an average diameter of 20 nm is used, the spherical voids in the electrocatalyst will typically have a diameter of approximately 20 nm. Those of skill in the art will be familiar with a variety of silica particles that are commercially available, and such particles may be used. Alternatively, known methods of forming silica particles may be employed in order to obtain particles of the desired shape and/or size.

As stated above, after deposition and/or impregnation of the imidazole and metal precursors on the support, the material is heat treated either in an inert atmosphere such as $N_2$, Ar, or He, or in a reactive atmosphere such as $NH_3$ or acetonitrile. Inert atmospheres are typically used when the infused materials are nitrogen rich, as the inert atmosphere enables the production of a high number of active sites with Fe (or other metal) $N_4$ centers. However, it may be desired to use a nitrogen rich atmosphere if the infused material is rich in carbon and depleted in nitrogen, as the nitrogen rich atmosphere will enable production of the Fe (or other metal) $N_4$ centers. As described in greater detail in the experimental section below, according to some preferred embodiments, the materials of the present are subjected to heat treatment in a reactive atmosphere.

According to some embodiments, particularly embodiments wherein a single step synthesis method is used, optimal temperatures for heat treatment are typically between 500° C. and 1100° C. According to some embodiments, heat treatment may preferably be between 750° C. and 900° C., or more preferably between 775° C. and 825° C. In some embodiments, heat treatment of around 800° C. is preferred, as our experimental data showed this temperature to produce catalysts having a high amount of catalytic activity for certain specific materials (see experimental section below).

If a sacrificial support is used, the sacrificial support is removed after heat treatment using suitable means. For example, the sacrificial support may be removed via chemical etching. Examples of suitable etchants include NaOH, KOH, and HF. According to some embodiments, it may be preferable to use KOH, as it preserves all metal and metal oxide in the catalyst and, if the species are catalytically active, use of KOH may, in fact, increase catalytic activity. Alternatively, in some embodiments, HF may be preferred as it is very aggressive and can be used to remove some poisonous species from the surface of the catalyst. Accordingly, those of skill in the art will be able to select the desired etchants based on the particular requirements of the specific catalytic material being formed.

As stated above, the presently described catalytic materials can also be synthesized using a two-step procedure. In this procedure, the imidazole and metal precursors are infused in the support, which is then subjected to a first heat treatment step, such as pyrolysis in order to produce an intermediate material that is rich with unreacted iron. The intermediate material is then subjected to a second heat treatment step, which may be, for example, a second pyrolysis treatment, resulting in newly formed active sites. If a sacrificial support is used, it is typically removed after the first heat treatment step using chemical etching or other suitable means as described above.

In embodiments utilizing a two-step procedure, and therefore, two separate heat treatment steps, it may be desirable for the different heat treatment steps to be conducted under different conditions, for example at different temperatures and/or for different durations of time. For example, the first heat treatment step may be performed at a higher temperature, such as 800° C. for 1 hr and the second heat treatment step may be performed at a temperature between 800 and 1000° C. for a period of time between 10 minutes and 1 hour.

It will be appreciated that some in some applications a mono-metallic catalyst may not be sufficiently stable or active to replace traditional platinum- or platinum alloy-based catalysts. Accordingly, as indicated above, according to some embodiments, the presently described method may incorporate the use of precursors of multiple metals in order to achieve a desired stability and/or activity.

According to another embodiments, the methods described above may be used to produce a metal organic framework, commonly referred to as a MOF. In this embodiments, the MOF-hybrids are formed by infusing a sacrificial support with imidazole-derived precursors with soluble metal salts under refluxing conditions. An example of suitable refluxing conditions include, for example, boiling solvents at greater than 120° C. for greater than 24 hours. The resulting material is then heat treated and the sacrificial support removed, as described above. While the imidazole-derived MOF is useful as a M-N—C catalyst, as described in detail in the examples section, it will be appreciated that the imidazole-derived MOF may have utility in other application as well, including hydrogen storage, absorbents, and supercapacitors.

According to some embodiments, it may be desirable to produce large amounts of the materials and/or catalysts described herein, for example in a batch-wise process. Accordingly, the present disclosure further provides a method for large-scale preparation of the presently described catalysts. According to an embodiment, the present disclosure provides a method which combines a sacrificial support-based methodology with spray pyrolysis to produce self-supported catalysts. According to this method, the spray pyrolysis method is a continuous method while the sacrificial support-based methodology is performed batch-wise. According to an exemplary method, the imidazole and metal precursor materials described herein are mixed with a sacrificial support, atomized, and dried in a tube furnace. The powder obtained from this procedure is then collected on a filter. The collected powder is then heat treated. Finally, the sacrificial support is removed, for example by leaching with HF or KOH.

It will be appreciated that the above-described large-scale production method is suitable for use for a wide variety of precursors and materials and thus not necessarily limited to the catalysts disclosed herein.

According to yet another method, the imidazole-derived materials are formed using a mechanochemical synthesis-based method, which is suitable for both small scale and large-batch production of imidazole-based materials. The method employs ball-milling or use of a high energy homogenizer and may or may not utilize a support, which may or may not be sacrificial.

Ball-milling has been described previously as a method for filling the pores of a carbon support with a pore-filler. See e.g., Jaouen et al. [44]. However, in the methods described in the present disclosure, ball-milling is used to enable mechanochemical synthesis, alleviating the need for solvent-based preparation methods. For the purposes of the present disclosure, the term "ball mill" is used to refer to any type of grinder that uses a grinding media to grind materials into fine powders and/or introduce to the system energy enough for starting chemical reaction. In general, for the purposes of the present disclosure, the ball mill used should be capable of producing enough to initiate the desired chemical reaction or achieve the desired level of mixing.

In general, the presently described methods utilize the energy produced by ball-milling of the various precursor materials to drive a chemical reaction between the precursors. According to a more specific example, a catalytic material according to the present disclosure may be synthesized by ball milling imidazole and metal precursors under sufficient conditions to initiate a chemical reaction between the various reactants. As with the above-described methods, the polymer is then subjected to heat treatment, (such as pyrolysis) in an inert ($N_2$, Ar, He, etc.) or reactive ($NH_3$, acetonitrile, etc.) atmosphere at a sufficient temperature to produce a catalytic material. According to some embodiments, the entire process is performed dry, by which is meant, without the presence of any solvents. According to one embodiment of a solvent-free process, all reactants (i.e. precursors) are combined in a ball mill in powder form and the entire process is conducted without the addition of any liquids. For the purposes of the present disclosure, a powder is a dry, bulk solid composed of a large number of very fine particles that may flow freely when shaken or tilted.

According to some embodiments the various precursors are ball-milled in the presence of supporting material so as to enable infusion of the precursors on, around, and throughout (if the supporting material is porous) the supporting material. Examples of suitable supporting materials include, but are not limited to carbon blacks, carbon nanotubes, graphene, graphene oxide, fullerene, etc. According to some embodiments the supporting material may be a sacrificial support.

Because the method can be practiced without the presence of any solvents, the method enables the synthesis of catalysts including insoluble materials. Examples of insoluble materials which can be included in catalysts according to the present disclosure include, but are not limited to, urea-melamine-formaldehyde polymer, melamine, Metal Organic Frameworks (MOFs), polyacrylonitrile, carbon, etc.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a catalyst" includes a plurality of such catalysts, and so forth.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Additional information may be gathered from the Examples section below. The reaction tests shown and described in the drawings and in the following examples clearly demonstrate that catalysts prepared using the method described possess high Oxygen Reduction activity in acid media. Further, the mechanism of oxygen reduction shows the direct reduction of oxygen to water by a 4 electron pathway, preventing corrosive peroxide production and therefore improving stability and durability of catalysts. Thus, catalysts of the composition and using the preparation method described herein, including but not limited to the described materials shown herein, are effective catalysts for oxygen reduction.

Experimental Data:

Fe-Imidazole catalysts were prepared as follows: First, a calculated amount of silica (Cab-O-Sil® M75D, surface area 90 $m^2$ $g_{-1}$) was dispersed in water by a high energy ultrasound probe. Then, a solution of imidazole in acetone was added to the silica and ultrasonicated for 20 minutes in an ultrasound bath. Finally, a solution of iron nitrate (Fe $(NO_3)_3*9H_2O$, Sigma-Aldrich) was added to $SiO_2$-Imidazole solution and ultrasonicated for 8 hours (the total metal loading on silica was calculated as ~20 wt. %). After ultrasonication, the resulting viscous gel of silica and Fe-Imidazole was dried overnight at T=85° C. The resulting solid material was ground to a fine powder in an agate mortar, and then subjected to heat treatment (HT). The general conditions of HT were UHP nitrogen (flow rate 100 cc $min^{-1}$), 20 deg $min^{-1}$ temperature ramp rate. The experimental variable component of heat-time trajectory (temperatures and duration of HT) were 900° C., 1 hour; 950° C., 30 minutes and 950° C., 1 hour. After heat treatment, the silica was leached by means of 25 wt. % HF overnight. Finally Fe-Imidazole was washed with DI water until neutral pH and dried at T=85° C. A second heat treatment was performed at T=950° C. in reactive ($NH_3$) atmospheres.

Figure 1:
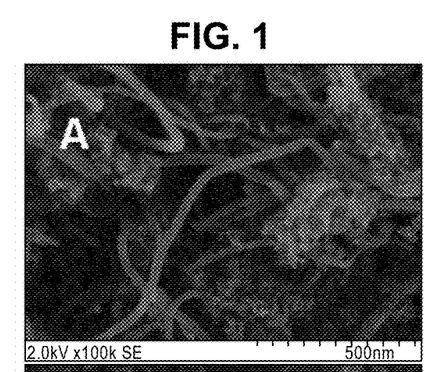
FIG. 1 is a SEM of an Fe-Benzimidazole (Fe-BZIM) catalyst after a single heat treatment step.
Figure 2:
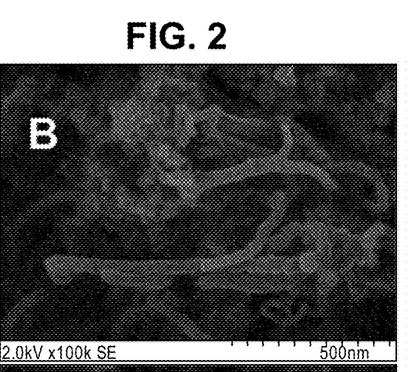
FIG. 2 is a SEM of an Fe-BZIM catalyst after double heat treatment (DHT) in a $H_2$ atmosphere.
Figure 3:
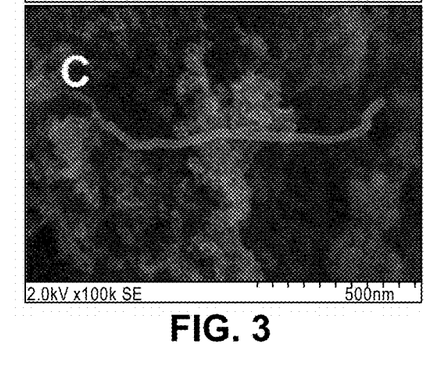
FIG. 3 is a SEM of an Fe-BZIM catalyst after double heat treatment in a $N_2$ atmosphere.
Figure 4:
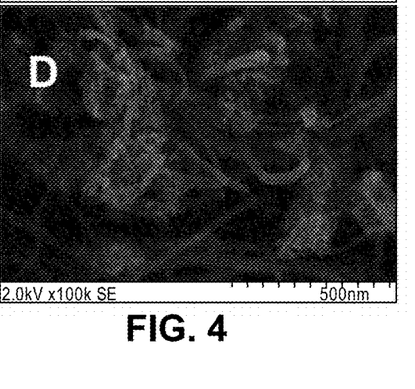
FIG. 4 is a SEM of an Fe-BZIM catalyst after double heat treatment in $NH_3$.

FIGS. 1-4 are SEM images of the Fe-BZIM catalysts prepared above. FIG. 1 is a SEM of an Fe-BenzImidazole (Fe-BZIM) catalyst after a single heat treatment step. FIG. 2 is a SEM of an Fe-BZIM catalyst after double heat treatment (DHT) in a $H_2$ atmosphere. FIG. 3 is a SEM of an Fe-BZIM catalyst after double heat treatment in a $N_2$ atmosphere. FIG. 4 is an SEM of an Fe-BZIM catalyst after double heat treatment in $NH_3$.

Figure 5:
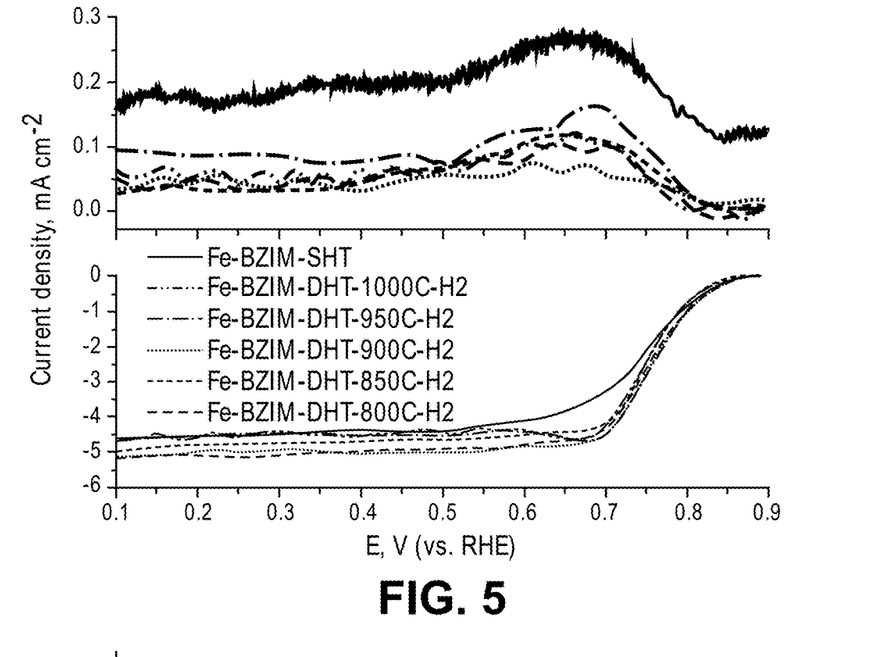
FIG. 5 is RRDE data for the Fe-BZIM catalyst treated in $H_2$ atmosphere.
Figure 6:
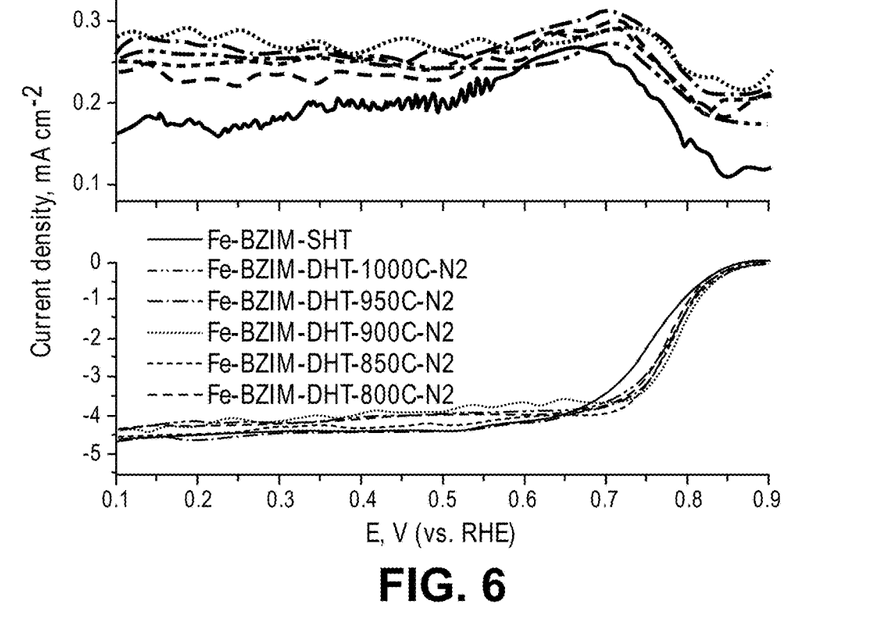
FIG. 6 is RRDE data for the Fe-BZIM catalyst after double heat treatment in a $N_2$ atmosphere.
Figure 7:
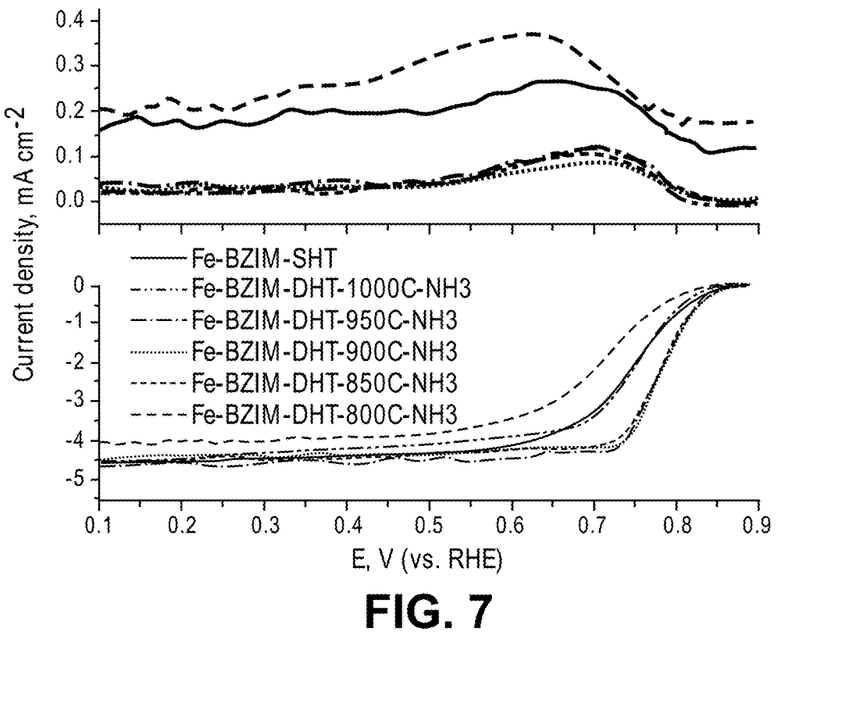
FIG. 7 is a SEM of an Fe-BZIM catalyst after double heat treatment in an $NH_3$ atmosphere.

FIGS. 5-7 are RRDE data for the Fe-BZIM catalysts. FIG. 5 is RRDE data for the Fe-BZIM catalyst treated in $H_2$ atmosphere. FIG. 6 is RRDE data for the Fe-BZIM catalyst after double heat treatment in a $N_2$ atmosphere. FIG. 7 is an SEM of an Fe-BZIM catalyst after double heat treatment in an $NH_3$ atmosphere. Conditions were: 0.5M $H_2SO_4$ saturated with 02, 1200 RPM, 5 mV $s^{-1}$, catalyst loading 0.6 mg $cm^{-2}$.

Figure 8:
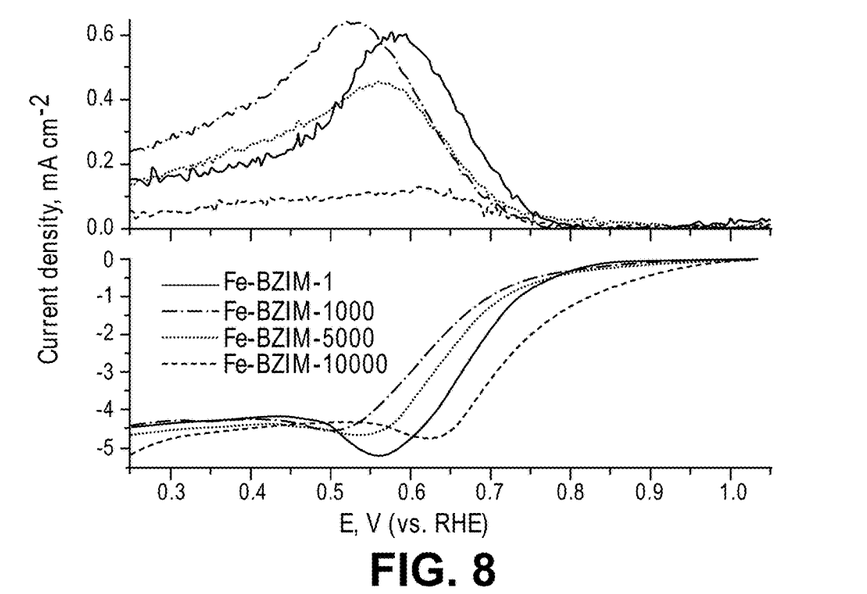
FIG. 8 shows DoE durability data by the RDE method for Fe-BZIM after double heat treatment in $N_2$ atmosphere.
Figure 9:
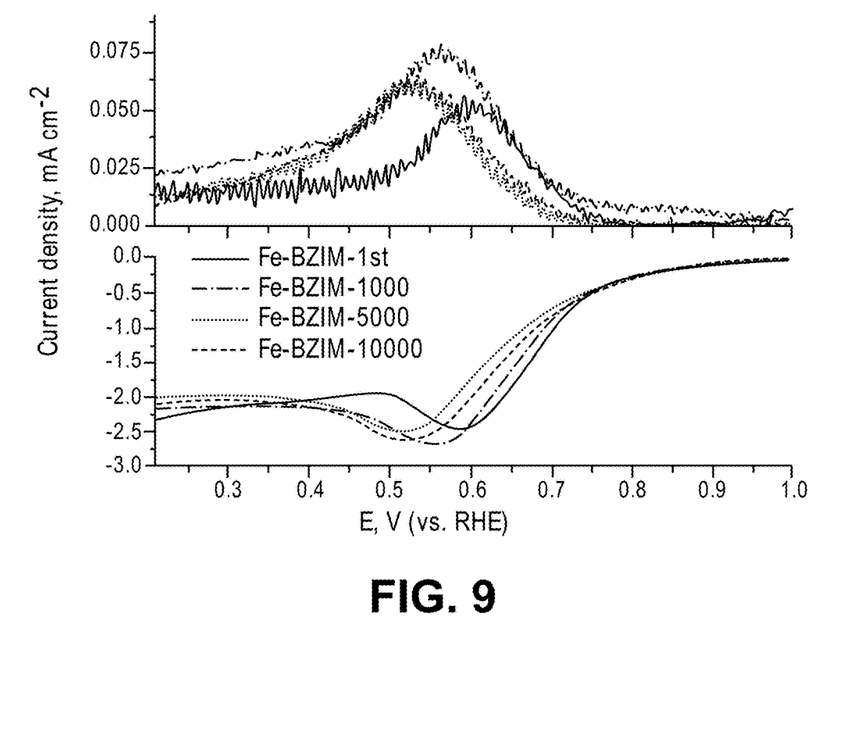
FIG. 9 also shows DoE durability data by the RDE method for Fe-BZIM after double heat treatment in $N_2$ atmosphere.

FIGS. 8 and 9 show DoE durability data by the RDE method for Fe-BZIM after double heat treatment in $N_2$ atmosphere. Conditions were: 0.1M $H_2SO_4$ saturated with $O_2$, 900 RPM, 50 mV $s^{-1}$, catalyst loading 0.2 mg $cm^{-2}$.

Figure 10:
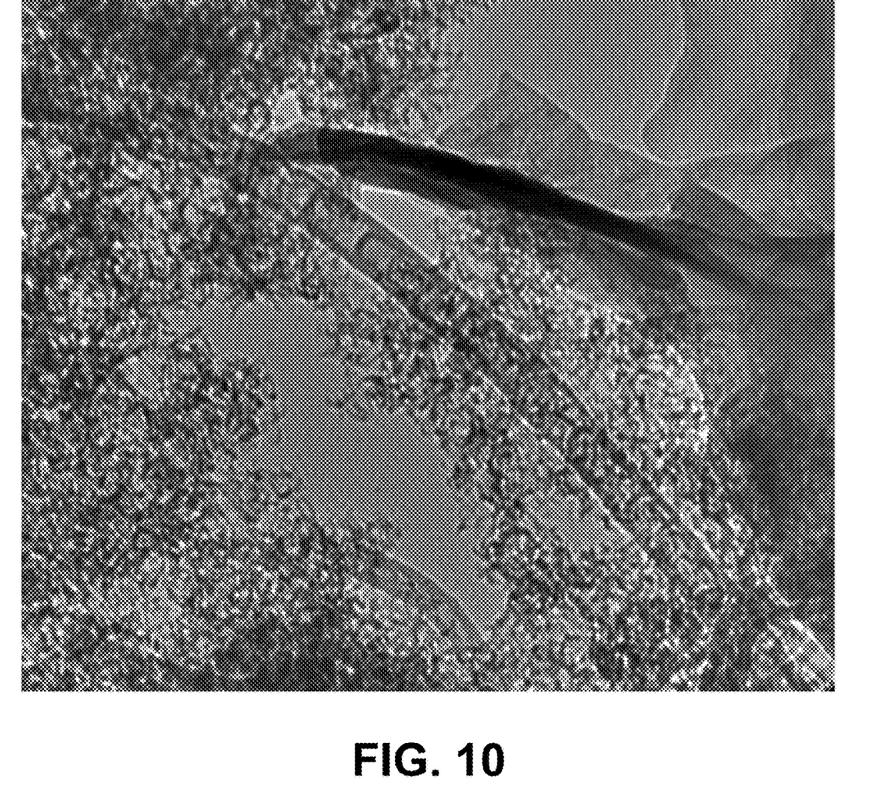
FIG. 10 is a TEM image of an Fe-BZIM catalyst.

FIG. 10 is a TEM image of the Fe-BZIM

Figure 11:
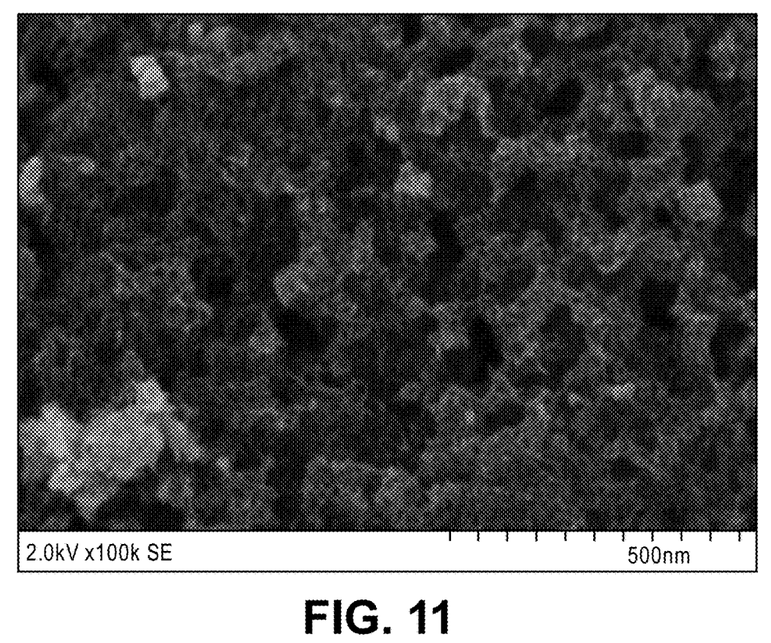
FIG. 11 is a SEM image of Fe-AminoBenzImidazole (Fe-ABZIM) derived catalyst.
Figure 12:
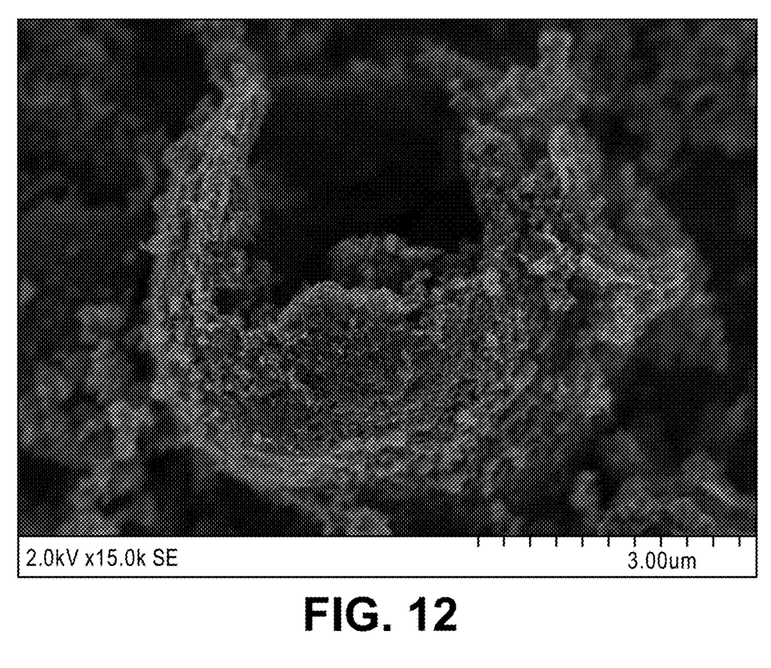
FIG. 12 is a higher magnification SEM image of an Fe-AminoBenzImidazole catalyst.

FIGS. 11 and 12 are SEM images of Fe-AminoBenzImidazole derived catalysts prepared as described above but substituting AminoBenzImidazole as the Imidazole.

Figure 13:
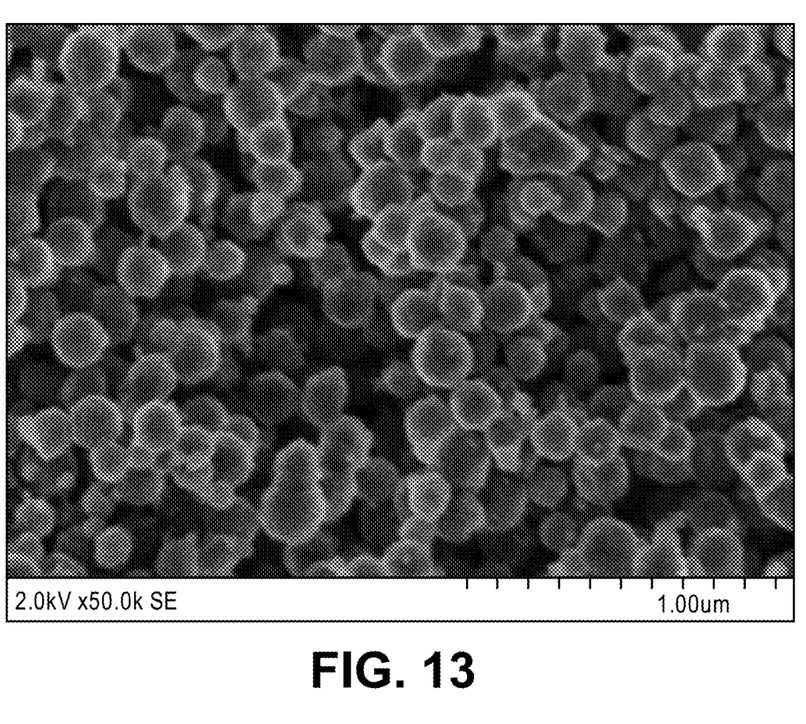
FIG. 13 is a SEM image of Fe-MethylImidazole prepared as described above but substituting MethylImidazole with the Imidazole.

FIG. 13 is a SEM image of Fe-MethylImidazole prepared as described above but substituting MethylImidazole with the Imidzole. The SEM image was taken before the high temperature treatment.

What is claimed is:

1. A method for forming a material comprising:
providing precursors of imidazole, a derivative of imidazole, or an imidazole family member and a transition metal;
interacting the imidazole, derivative of imidazole, or imidazole family member and transition metal precursors in the presence of a supporting material so as to enable the imidazole, derivative of imidazole, or imidazole family member, and transition metal precursors to form around and/or infuse the supporting material; and
heat treating the dispersed precursors.

2. The method of claim 1 wherein the step of interacting comprises depositing precursors on the supporting material.

3. The method of claim 1 wherein the step of interacting comprises impregnating the supporting material with the precursors.

4. The method of claim 3 wherein the sacrificial support is porous and the imidazole and transition metal precursors impregnate the pores of the sacrificial support.

5. The method of claim 4 wherein the sacrificial support is silica.

6. The method of claim 1 wherein the supporting material is a sacrificial support and the method further comprises removing the sacrificial support after the step of heat treating.

7. The method of claim 6 further comprising ball-milling the imidazole and transition metal precursors in the presence of a supporting material.

8. The method of claim 7 wherein the supporting material comprises carbon.

9. The method of claim 7 wherein the supporting material consists of carbon.

10. The method of claim 7 wherein the sacrificial support is silica.

11. The method of claim 6 further comprising a second heat treatment after the sacrificial support is removed.

12. The method of claim 1 further comprising ball-milling the imidazole and transition metal precursors in the presence of a supporting material.

13. The method of claim 12 wherein the sacrificial support is silica.

14. The method of claim 1 wherein heat treating the dispersed precursors comprises pyrolysis.

15. The method of claim 1 wherein the imidazole, derivatives of imidazole, or imidazole family member is selected from the group consisting of Benzimidazole, AminoBenzimidazole, and Methylimidazole.

* * * * *